United States Patent [19]
Hashizume et al.

[11] Patent Number: 5,869,684
[45] Date of Patent: Feb. 9, 1999

[54] METHOD FOR PRODUCING PYRAZOLINONE COMPOUNDS

[75] Inventors: Masaya Hashizume; Mitsuru Sasaki, both of Hyogo, Japan

[73] Assignee: Sumitomo Chemical Company, Limited, Osaka, Japan

[21] Appl. No.: 76,763

[22] Filed: May 13, 1998

[30] Foreign Application Priority Data

Jul. 7, 1997 [JP] Japan .................................. 9-181069

[51] Int. Cl.⁶ ................................................. C07D 231/52
[52] U.S. Cl. ........................................................ 548/368.7
[58] Field of Search ........................................... 548/368.7

[56] References Cited

FOREIGN PATENT DOCUMENTS 0679643  11/1995  European Pat. Off. .

*Primary Examiner*—Robert W. Ramsuer
*Attorney, Agent, or Firm*—Sughrue, Mion, Zinn, Macpeak & Seas, PLLC

[57] ABSTRACT

A method for producing a pyrazolinone compound represented by the formula (I):

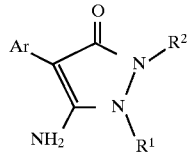

(wherein, $R^1$ is a hydrocarbyl group which may be substituted, $R^2$ is a hydrocarbyl group which may be substituted and Ar is a phenyl group which may be substituted) which comprises reacting a lithium salt of a pyrazolinone compound represented by the formula (II):

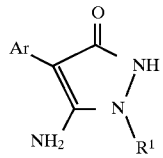

(wherein, $R^1$ and Ar have the same meanings as described above) is reacted with a sulfonic acid ester represented by the formula (III):

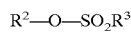

$$R^2\text{—}O\text{—}SO_2R^3$$

(wherein, $R^2$ has the same meaning as described above and $R^3$ is a $C_1$–$C_{10}$ alkyl group or a phenyl group which may be substituted) in the presence of an ether solvent.

8 Claims, No Drawings

METHOD FOR PRODUCING PYRAZOLINONE COMPOUNDS

FIELD OF THE INVENTION

The present invention relates to a method for producing pyrazolinone compounds.

PRIOR ARTS

The pyrazolinone compounds represented by the followings:

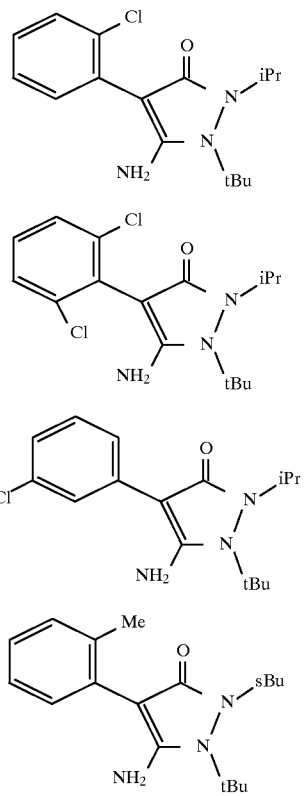

(wherein, iPr represents an isopropyl group, tBu represents a tert-butyl group, sBu represents a sec-butyl group and Me represents a methyl group: hereinafter the same) and the like are known to have excellent plant disease controlling activity, and as a concrete method for producing the same, alkylation processes represented by the following schemes are known (Japanese Patent Application Laid-Open No. Hei-8-208621-A). Schemes:

Production Method 1

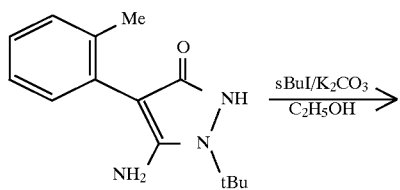

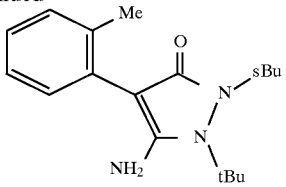

Production method 2

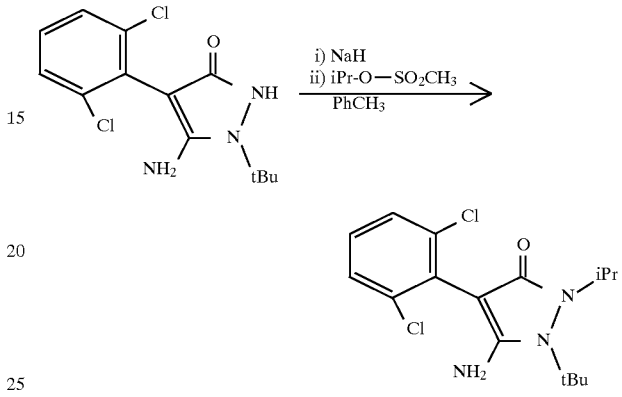

However, in these production methods, an alkylated compound on a carbonyl oxygen at 3-position of a pyraozlinone ring (hereinafter, referred to as an O-alkyl compound) for example, a compound represented by the followings:

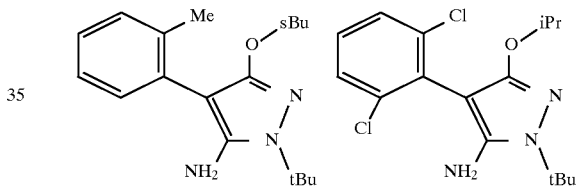

may be by-produced in a large amount in addition to a desired compound in which nitrogen at 2-position of a pyrazolinone ring is alkylated (hereinafter, referred to as a N-alkyl compound) (see, Comparative Examples 1 and 2 described below), and a more advantageous production method is desired to be developed for improving the yield and regioselectivity of the alkylation.

DETAILED DESCRIPTION OF THE INVENTION

The present inventors have intensely studied to solve the above-described problem, and found that, by reacting a lithium salt of a pyrazolinone compound represented by the formula (I):

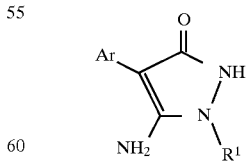

(wherein, $R^1$ is a hydrocarbyl group which may be substituted, and Ar is a phenyl group which may be substituted) with a sulfonic acid ester represented by the formula (II):

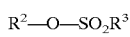

(wherein, $R^2$ is a hydrocarbyl group which may be substituted and $R^3$ is a $C_1$–$C_{10}$ alkyl group or a phenyl group which may be substituted) in the presence of an ether solvent, formation of an O-alkyl compound is remarkably inhibited and a pyrazolinone compound represented by the formula (III):

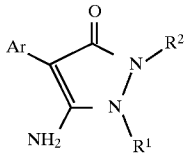

(wherein, $R^1$, $R^2$ and Ar have the same meanings as described above) can be obtained in high yield with high regioselectivity. Namely, the formation of an O-alkyl compound is markedly reduced.

Thus, the present invention provides a method for producing a pyrazolinone compound represented by the formula (III), which comprises reacting a lithium salt of a pyrazolinone compound represented by the formula (I) with a sulfonic acid ester represented by the formula (II) in the presence of an ether solvent (hereinafter, referred to as the present invention process).

The present invention is described in detail below.

The phenyl group which may be substituted, represented by Ar in the general formulae (I) and (III) is, for example, shown by the following formula (V):

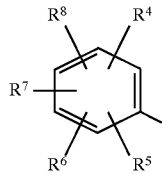

(wherein, $R^4$ to $R^8$ may be the same or different and are a hydrogen atom, halogen atom, alkyl group, haloalkyl group, alkoxy group, alkoxyalkyl group, alkoxyalkoxy group, haloalkoxy group, alkylthio group, haloalkylthio group, cyano group, nitro group, phenyl group which may be substituted, or phenoxy group which may be substituted, or adjacent two groups of $R^4$ to $R^8$ are bonded at each end to form a group represented by CH=CH—CH=CH, methylenedioxy group which may be substituted with at least one halogen atom or alkylene group which may contain one oxygen atom and may be substituted with at least one alkyl group).

Regarding the moieties represented by $R^4$ to $R^8$, examples of the halogen atom include a fluorine atom, chlorine atom, bromine atom and iodine atom, examples of the alkyl group include $C_1$–$C_5$ alkyl groups (for example, a methyl group, ethyl group, propyl group, isopropyl group and tert-butyl group), examples of the haloalkyl group include $C_1$–$C_5$ alkyl groups which are substituted with the same or different 1 to 11 halogen atoms (for example, a trifluoromethyl group, tetrafluoroethyl group and heptafluoropropyl group), examples of the alkoxy group include $C_1$–$C_5$ alkoxy groups (for example, a methoxy group, ethoxy group, propoxy group and isopropoxy group), examples of the alkoxyalkyl group include $C_1$–$C_3$ alkoxy $C_1$–$C_3$ alkyl groups (for example, methoxymethyl group), examples of the alkoxyalkoxy group include $C_1$–$C_3$ alkoxy $C_1$–$C_3$ alkoxy groups (for example, methoxymethoxy group), examples of the haloalkoxy group include $C_1$–$C_5$ alkoxy groups which are substituted with the same or different 1 to 11 halogen atoms (for example, a trifluoromethoxyl group, difluoromethoxyl group and tetrafluoroethoxyl group), examples of the alkylthio group include $C_1$–$C_5$ alkylthio groups (for example, a methylthio group and ethylthio group), examples of the haloalkylthio group include $C_1$–$C_5$ alkylthio groups which are substituted with the same or different 1 to 11 halogen atoms (for example, a trifluoromethylthio group), the phenyl group which may be substituted means a phenyl group which may be substituted with the same or different 1 to 5 substituents, the phenoxy group which may be substituted means a phenoxy group which may be substituted with the same or different 1 to 5 substituents, {examples of the substituents on the phenyl or phenoxy groups which may be substituted include, for example, halogen atoms (a fluorine atom, chlorine atom, bromine atom, iodine atom), $C_1$–$C_5$ alkyl groups (for example, a methyl group and ethyl group), $C_1$–$C_5$ alkoxy groups (for example, a methoxy group and ethoxy group), $C_1$–$C_5$ alkylthio groups (for example, a methylthio group and ethylthio group), $C_1$–$C_5$ haloalkyl groups, preferably $C_1$–$C_2$ haloalkyl groups (for example, trifluoromethyl group), $C_1$–$C_5$ haloalkoxy group, preferably $C_1$–$C_2$ haloalkoxyl groups (for example, a trifluoromethoxy group and difluoromethoxy group), $C_1$–$C_5$ haloalkylthio group, preferably $C_1$–$C_2$ haloalkylthio groups (for example, a trifluoromethylthio group) and cyano group}, examples of the methylenedioxy group which may be substituted include a methylenedioxy group, difluoromethylenedioxy group, and examples of the alkylene group (for example, a $C_2$–$C_6$ alkylene group) which may contain one oxygen atom and may be substituted with an alkyl group (for example, a $C_1$–$C_4$ alkyl group such as a methyl group) include a trimethylene group, tetramethylene group, a group represented by $OCH_2CH_2$ and a group represented by $OCH_2CH(CH_3)$.

Examples of the hydrocarbyl group which may be substituted represented by $R^1$ in the formulae (I) and (III) include $C_1$–$C_{10}$ alkyl groups (for example, an ethyl group, propyl group, isopropyl group, butyl group, isobutyl group, sec-butyl group, 2-methylbutyl group, 2-ethylpropyl group and tert-butyl group), $C_2$–$C_{10}$ alkenyl groups (for example, 1-methyl-2-propenyl group), $C_2$–$C_{10}$ alkynyl groups (for example, 1-methyl-2-propynyl group), $C_1$–$C_{10}$ alkyl groups substituted with the same or different 1 to 21 halogen atoms, $C_2$–$C_{10}$ alkenyl groups substituted with the same or different 1 to 19 halogen atoms, $C_2$–$C_{10}$ alkynyl groups substituted with the same or different 1 to 17 halogen atoms, $C_1$–$C_5$ alkoxy $C_1$–$C_5$ alkyl groups (for example, a methoxymethyl group and 1-methoxyethyl group), $C_1$–$C_5$ alkylthio $C_1$–$C_5$ alkyl groups (for example, a methylthiomethyl group and 1-methylthioethyl group), $C_1$–$C_5$ alkyl groups substituted with the same or different 1 to 11 halogen atoms having a $C_1$–$C_5$ alkoxy group substituted with the same or different 1 to 11 halogen atoms, $C_1$–$C_5$ alkyl groups substituted with the same or different 1 to 11 halogen atoms having a $C_1$–$C_5$ alkylthio group substituted with the same or different 1 to 11 halogen atoms, $C_1$–$C_5$ alkyl groups substituted with a cyano group (for example, 1-cyanoethyl group), $C_1$–$C_5$ alkyl groups substituted with a $C_1$–$C_5$ alkoxycarbonyl group (for example, 1-(methoxycarbonyl)ethyl group), $C_3$–$C_8$ cycloalkyl groups which may be substituted with at least one halogen atom and may contain an unsaturated bond (for example, a cyclohexyl group and cyclopentyl group), phenyl group which may be substituted with the same or different 1 to 5 substituents {examples of the substituent include halogen atoms (a fluorine atom, chlorine atom, bromine atom, iodine atom), $C_1$–$C_5$ alkyl groups (for example, a methyl group and ethyl group), $C_1$–$C_5$ alkoxy groups (for example, methoxy group and ethoxy group), $C_1$–$C_5$ alkylthio groups (for example, a methylthio group and ethylthio group), $C_1$–$C_5$ haloalkyl groups, preferably $C_1$–$C_2$ haloalkyl groups (for example, trifluoromethyl group), $C_1$–$C_5$ haloalkoxy group, preferably $C_1$–$C_2$ haloalkoxyl groups (for example, a trifluoromethoxy group and difluoromethoxy group), $C_1$–$C_5$ haloalkylthio group, preferably $C_1$–$C_2$ haloalkylthio groups (for example, a trifluoromethylthio group) and cyano group}, $C_7$–$C_{17}$ aralkyl groups which may be substituted with the same or different 1 to 5 substituents (for eample, a benzyl group, α-methylbenzyl group and α,α-dimethylbenzyl group) {examples of the substituent include halogen atoms (a fluorine atom, chlorine atom, bromine atom, iodine atom), $C_1$–$C_5$ alkyl groups (for example, a methyl group and ethyl group), $C_1$–$C_5$ alkoxy groups (for example, methoxy group and ethoxy group), $C_1$–$C_5$ alkylthio groups (for example, a methylthio group and ethylthio group), $C_1$–$C_5$ haloalkyl groups, preferably $C_1$–$C_2$ haloalkyl groups (for example, trifluoromethyl group), $C_1$–$C_5$ haloalkoxy group, preferably $C_1$–$C_2$ haloalkoxyl groups (for example, a trifluoromethoxy group and difluoromethoxy group), $C_1$–$C_5$ haloalkylthio group, preferably $C_1$–$C_2$ haloalkylthio groups (for example, a trifluoromethylthio group) and cyano group}.

Examples of the hydrocarbyl group which may be substituted represented by $R^2$ in the formulae (II) and (III) include $C_1$–$C_{10}$ alkyl groups (for example, an ethyl group, propyl group, isopropyl group, butyl group, isobutyl group, sec-butyl group, 2-methylbutyl group and 2-ethylpropyl group), $C_2$–$C_{10}$ alkenyl groups (for example, 1-methyl-2-propenyl group), $C_2$–$C_{10}$ alkynyl groups (for example, 1-methyl-2-propynyl group), $C_1$–$C_{10}$ alkyl groups substituted with the same or different 1 to 21 halogen atoms, $C_2$–$C_{10}$ alkenyl groups substituted with the same or different 1 to 19 halogen atoms, $C_2$–$C_{10}$ alkynyl groups substituted with the same or different 1 to 17 halogen atoms, $C_1$–$C_5$ alkoxy $C_1$–$C_5$ alkyl groups (for example, a 1-methyl-2-methoxyethyl group), $C_1$–$C_5$ alkylthio $C_1$–$C_5$ alkyl groups (for example, a 1-methyl-2-methylthioethyl group), $C_1$–$C_5$ alkyl groups substituted with the same or different 1 to 11 halogen atoms having a $C_1$–$C_5$ alkoxy group substituted with the same or different 1 to 11 halogen atoms, $C_1$–$C_5$ alkyl groups substituted with the same or different 1 to 11 halogen atoms having a $C_1$–$C_5$ alkylthio group substituted with the same or different 1 to 11 halogen atoms, $C_1$–$C_5$ alkyl groups substituted with a cyano group (for example, 1-methyl-2-cyanoethyl group), $C_1$–$C_5$ alkyl groups substituted with a $C_1$–$C_5$ alkoxycarbonyl group (for example, 2-methoxycarbonylethyl group), $C_3$–$C_8$ cycloalkyl groups which may be substituted with at least one halogen atom and may contain an unsaturated bond (for example, a cyclohexyl group and cyclopentyl group), $C_7$–$C_{17}$ aralkyl groups which may be substituted with the same or different 1 to 5 substituents (for eample, a benzyl group and α-methylbenzyl group) {examples of the substituent include halogen atoms (a fluorine atom, chlorine atom, bromine atom, iodine atom), $C_1$–$C_5$ alkyl groups (for example, a methyl group and ethyl group), $C_1$–$C_5$ alkoxy groups (for example, methoxy group and ethoxy group), $C_1$–$C_5$ alkylthio groups (for example, a methylthio group and ethylthio group), $C_1$–$C_5$ haloalkyl groups, preferably $C_1$–$C_2$ haloalkyl groups (for example, trifluoromethyl group), $C_1$–$C_5$ haloalkoxy group, preferably $C_1$–$C_2$ haloalkoxyl groups (for example, a trifluoromethoxy group and difluoromethoxy group), $C_1$–$C_5$ haloalkylthio group, preferably $C_1$–$C_2$ haloalkylthio groups (for example, a trifluoromethylthio group) and cyano group}.

Regarding $R^3$ in the formula (II), examples of the $C_1$–$C_{10}$ alkyl include a methyl group, ethyl group, propyl group, isopropyl group and tert-butyl group, and examples of the phenyl group which may be substituted include a phenyl group, 2-methylphenyl group, 3-methylphenyl group, 4-methylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-fluorophenyl group, 2-chlorophenyl group, 3-chlorophenyl group, 4-chlorophenyl group, 2-bromophenyl group, 3-buromophenyl group and 4-bromophenyl group.

The present invention process is conducted by reacting the lithium salt of the pyrazolinone compound represented by the formula (I) with the sulfonic acid ester represented by the formula (II) in the presence of an ether solvent.

The reaction temperature for this reaction is usually in the range of 60° to 150° C., preferably 80° to 120° C., and the reaction time is usually in the range of 1 to 12 hours.

The amount of the sulfonic acid ester represented by the formula (II) used in the reaction is usually from 1.0 to 5.0 mol, preferably from 1.1 to 2.0 mol based on 1 mol of the lithium salt of the pyrazolinone compound represented by the formula (I).

The ether solvent used in the present invention means a reaction solvent having at least one ether bond (—C—O—C—). Examples of the ether solvent include 1,4-dioxane, tetrahydrofuran, tetrahydropyran and diisopropyl ether, and 1,4-dioxane, tetrahydrofuran and tetrahydropyran are preferred.

The present invention process can be conducted in the ether solvent alone or in the mixture of the ether solvent and the other inert solvent. In case the mixed solvent is used, it usually contain the ether solvent in an amount of 50 vol % or more. Examples of the other inert solvent include, for example, aromatic hydrocarbons such as benzene, toluene, xylene and chlorobenzene and aliphatic hydrocarbons such as hexane.

The concentration of the lithium salt of the pyrazolinone compound represented by the formula (I) is usually 0.01 to 2M, preferably 0.05 to 1M in the reaction solution according to the present invention process.

The pyrazolinone compound represented by the formula (III) can be obtained by conducting usual work-up such as adding water to the reaction mixture after completion of the reaction, then, extracting the mixture with an organic solvent, and condensation by removing solvent. This compound can optionally also be purified by means of washing with an organic solvent, recrystallization and column chromatography.

The sulfonic acid ester represented by the formula (II) used in the present invention process can be prepared according to a method described in J. Org. Chem., (1970), 35(9), 3195.

The lithium salt of the pyrazolinone compound represented by the formula (I) can be produced by reacting the pyrazolinone compound represented by the formula (I) with an anhydrous lithium hydroxide or lithium hydroxide monohydrate under azeotropic dehydration condition, or by reacting the pyrazolinone compound represented by the formula (I) with lithium hydride, alkyllithium such as $C_1$–$C_6$ alkyllithium (for example, buthyllithium and sec-buthyllithium) or lithium dialkylamide such as lithium di($C_1$–$C_6$) alkylamide (for example, lithium diethylamide and lithium diisopropylamide).

When the pyrazolinone compound represented by the formula (I) is allowed to react with an anhydrous lithium hydroxide or lithium hydroxide monohydrate under azeotropic dehydration condition, the range of the reaction temperature for this reaction is usually from 80° to 140° C., and the range of the reaction time is usually from 0.5 to 12 hours.

The amount of the anhydrous lithium hydroxide or lithium hydroxide monohydrate is usually from 1.0 to 5.0 mol, preferably from 1.1 to 2.0 mol based on 1 mol of the pyrazolinone derivative represented by the formula (I).

As the solvent, aromatic hydrocarbons such as benzene, toluene, xylene, chlorobenzene and the like are listed.

When the pyrazolinone compound represented by the formula (I) is allowed to react with lithium hydride, alkyllithium or lithium dialkylamide, the range of the reaction time for this reaction is usually from 1 to 12 hours, and the range of the reaction temperature is usually from 60° to 120° C. when lithium hydride is used, and usually from −78° to 30° C. when alkyllithium or lithium dialkylamide is used.

The amount of the lithium hydride, alkyllithium or lithium dialkylamide is usually from 1.0 to 2.0 mol based on 1 mol of the pyrazolinone derivative represented by the formula (I).

As the solvent, aliphatic hydrocarbons such as hexane, aromatic hydrocarbons such as toluene, or ethers such as diethyl ether, 1,4-dioxane, tetrahydrofuran and tetrahydropyran, diisopropyl ether are shown.

The lithium salt of the pyrazolinone compound represented by the formula (I) can be obtained by distilling the solvent off under reduced pressure from the reaction mixture after completion of the reaction.

When ethers are used as a reaction solvent, the reaction solution after completion of the reaction can be used for the present invention process without further operation.

The pyrazolinone compound represented by the formula (I) used in the above-described production method can be prepared according to a method described in EP-679643-A.

EXAMPLES

The following examples further illustrate the present invention in detail, but do not limit the scope thereof.

Production Example 1

A reaction vessel equipped with a water separator was charged with 3.00 g of 1-tert-butyl-4-(2,6-dichlorophenyl)-5-amino-pyrazolin-3-one, 0.84 g of lithium hydroxide monohydrate and 15 ml of toluene, and the reaction mixture was stirred for 1 hour under azeotropic dehydration condition, then, toluene was distilled off under reduced pressure.

To the residue was added 100 ml of 1,4-dioxane, and 2.77 g of isopropyl methanesulfonate in 15 ml of 1,4-dioxane was added dropwise to the reaction mixture under reflux. After completion of the addition, the mixture was heated for 3 hours under reflux condition, then, the solvent was distilled off, and 60 ml of water was added to the residue, and the mixture was extracted with 60 ml of ethyl acetate. The organic layer was washed with 60 ml of water, then, concentrated, to obtain 3.38 g of a yellow solid. The crude product analyzed by $^1$H-NMR on the ratio of N-alkyl compound to O-alkyl compound being 95 to 5 was washed with a mixed solvent of hexane:diethyl ether (20:1) to obtain 3.06 g (yield: 89.5%) of 1-tert-butyl-2-isopropyl-4-(2,6-dichlorophenyl)-5-amino-pyrazolin-3-one.

$^1$H-NMR (CDCl$_3$/TMS) δ value (ppm) 1.39 (d, 6H), 1.43 (s, 9H), 3.64 (q, 1H), 4.22 (s, 2H), 7.16 (d, 1H), 7.19 (d, 1H), 7.35 (d, 1H)

Production Example 2

A reaction vessel equipped with a water separator was charged with 3.68 g of 1-tert-butyl-4-(2-methylphenyl)-5-amino-pyrazolin-3-one, 1.26 g of lithium hydroxide monohydrate and 30 ml of toluene, and the reaction mixture was stirred for 1 hour under azeotropic dehydration condition, then, toluene was distilled off under reduced pressure.

To the residue was added 50 ml of 1,4-dioxane, and 3.04 g of sec-butyl methanesulfonate in 10 ml of 1,4-dioxane was added dropwise to the reaction mixture under reflux. After completion of the addition, the mixture was heated for 7 hours under reflux, then, the solvent was distilled off, and 60 ml of water was added to the residue, and the mixture was extracted with 60 ml of ethyl acetate. The organic layer was washed with 60 ml of water, then, concentrated, to obtain 4.02 g of a yellow solid. The crude product analyzed by $^1$H-NMR on the ratio of N-alkyl compound to O-alkyl compound being 80 to 20 was washed with a mixed solvent of hexane:diethyl ether (20:1) to obtain 3.07 g (yield: 67.9%) of 1-tert-butyl-2-sec-butyl-4-(2-methylphenyl)-5-amino-pyrazolin-3-one.

$^1$H-NMR (CDCl$_3$/TMS) δ value (ppm) 0.93 (t, 3H), 1.29 (d, 3H), 1.40 (s, 9H), 1.95 (m, 2H), 2.26 (s, 3H), 3.37 (q, 1H), 4.18 (s, 2H), 7.09 to 7.25 (m, 4H)

Comparative Example 1 (Production 1 According to the Scheme Described Above)

A mixture of 1.23 g of 1-tert-butyl-4-(2-methylphenyl)-5-amino-pyrazolin-3-one, 1.84 g of 2-iodobutane, 2.1 g of potassium carbonate and 20 ml of ethanol was heated under reflux for 10 hours. The solvent was distilled off under reduced pressure, then, water was added, and the mixture was extracted with ethyl acetate. The organic layer was dried over magnesium sulfate anhydride, then, the solvent was distilled off under reduced pressure. The residue was analyzed by $^1$H-NMR on the ratio of N-alkyl compound to O-alkyl compound being 16 to 84 was applied to column chromatography to obtain 250 ml (yield: 16%) of 1-tert-butyl-2-sec-butyl-4-(2-methylphenyl)-5-aminopyrazolin-3-one.

Comparative Example 2 (Production 2 According to the Scheme Described Above)

To 160 mg of sodium hydroxide (60% oil dispersion) were added 30 ml of toluene and 1.00 g of 1-tert-butyl-4-(2,6-dichlorophenyl)-5-amino-pyrazolin-3-one, and the mixture was heated for 2 hours at 100° C. To this was added 550 ml of isopropyl mathanesulfonate, and the mixture was heated for additional 3 hours at 100° C. After completion of the reaction, water was added, and the mixture was extracted with ethyl acetate. The organic layer was dried over magnesium sulfate anhydride, then, the solvent was distilled off under reduced pressure. The residue analyzed by $^1$H-NMR on the ratio of N-alkyl compound to O-alkyl compound being 31 to 69 was applied to column chromatography to obtain 353 mg (yield: 31%) of 1-tert-butyl-2-sec-butyl-4-(2,6-dichlorophenyl)-5-aminopyrazolin-3-one.

According to the present invention process, the pyrazolinone compound represented by the formula (III) can be produced in high yield with high selectivity.

What is claimed is:

1. A method for producing a pyrazolinone compound represented by the formula (I):

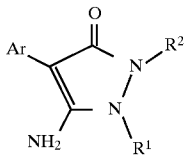

(wherein, $R^1$ is a hydrocarbyl group which may be substituted, $R^2$ is a hydrocarbyl group which may be substituted and Ar is a phenyl group which may be substituted) which comprises reacting a lithium salt of a pyrazolinone compound represented by the formula (II):

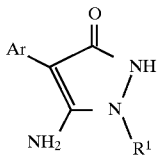

(wherein, $R^1$ and Ar have the same meanings as described above) is reacted with a sulfonic acid ester represented by the formula (III):

$$R^2-O-SO_2R^3$$

(wherein, $R^2$ has the same meaning as described above and $R^3$ is a $C_1$–$C_{10}$ alkyl group or a phenyl group which may be substituted) in the presence of an ether solvent.

2. The method according to claim 1, wherein the lithium salt of the pyrazolinone compound (I) is a lithium salt of a pyrazolinone compound represented by the formula (IV):

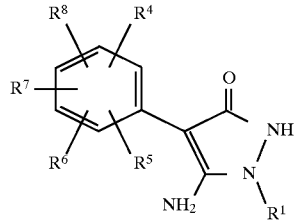

(wherein, $R^1$ has the same meaning as described above and $R^4$ to $R^8$ may be the same or different and are a hydrogen atom, halogen atom, alkyl group, haloalkyl group, alkoxy group, alkoxyalkyl group, alkoxyalkoxy group, haloalkoxy group, alkylthio group, haloalkylthio group, cyano group, nitro group, phenyl group which may be substituted, or phenoxy group which may be substituted, or adjacent two groups of $R^4$ to $R^8$ are bonded at each end to form a group represented by CH=CH—CH=CH, methylenedioxy group which may be substituted with at least one halogen atom or alkylene group which may contain one oxygen atom and may be substituted with at least one alkyl group).

3. The method according to claim 2, wherein $R^4$ to $R^8$ in the pyrazolinone compound (IV) may be the same or different and are a hydrogen atom, halogen atom, $C_1$–$C_5$ alkyl group, $C_1$–$C_5$ haloalkyl group, $C_1$–$C_5$ alkoxy group, $(C_1$–$C_3)$alkoxy $(C_1$–$C_3)$alkyl group, $(C_1$–$C_3)$alkoxy$(C_1$–$C_3)$ alkoxy group, $C_1$–$C_5$ haloalkoxy group, $C_1$–$C_5$ alkylthio group, $C_1$–$C_5$ haloalkylthio group, cyano group, nitro group, phenyl group (which may be substituted with at least one halogen atom, $C_1$–$C_5$ alkyl group, $C_1$–$C_5$ alkoxy group, $C_1$–$C_5$ alkylthio group, $C_1$–$C_5$ haloalkyl group, $C_1$–$C_5$ haloalkoxy group, $C_1$–$C_5$ haloalkylthio group or cyano group), or phenoxy group (which may be substituted with at least one halogen atom, $C_1$–$C_5$ alkyl group, $C_1$–$C_5$ alkoxy group, $C_1$–$C_5$ alkylthio group, $C_1$–$C_5$ haloalkyl group, $C_1$–$C_5$ haloalkoxy group, $C_1$–$C_5$ haloalkylthio group or cyano group), or, adjacent two groups of $R^4$ to $R^8$ are bonded at each end to form a group represented by CH=CH—CH=CH, methylenedioxy group which may be substituted with at least one halogen atom, trimethylene group, tetramethylene group, a group represented by $OCH_2CH_2$ or a group represented by $OCH_2CH(CH_3)$.

4. The method according to claim 1, wherein $R^2$ in the sulfonic acid ester (II) is an isopropyl group or sec-butyl.

5. The method according to claim 1, wherein $R^3$ in the sulfonic acid ester (II) is a methyl group, phenyl group or 4-methylphenyl group.

6. The method according to claim 1, wherein the ether solvent is 1,4-dioxane, tetrahydrofuran or tetrahydropyran.

7. The method according to claim 1, wherein the ether solvent is 1,4-dioxane, tetrahydrofuran or tetrahydropyran and $R^3$ in the sulfonic acid ester (II) is a methyl group, phenyl group or 4-methylphenyl group.

8. The method according to claim 1, wherein the reaction temperature is in the range of 60° to 150° C.

* * * * *